US007256183B2

(12) United States Patent
Peterson et al.

(10) Patent No.: US 7,256,183 B2
(45) Date of Patent: *Aug. 14, 2007

(54) METHOD FOR TREATING OR PREVENTING INFLAMMATORY DISEASES

(75) Inventors: Ward M. Peterson, Morrisville, NC (US); Benjamin R. Yerxa, Raleigh, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 637 days.

This patent is subject to a terminal disclaimer.

(21) Appl. No.: 10/290,213

(22) Filed: Nov. 6, 2002

(65) Prior Publication Data

US 2003/0125299 A1   Jul. 3, 2003

Related U.S. Application Data

(60) Provisional application No. 60/337,828, filed on Nov. 6, 2001.

(51) Int. Cl.
*A01N 43/04*   (2006.01)
*A61K 31/70*   (2006.01)

(52) U.S. Cl. ............................. 514/47; 514/48; 514/51

(58) Field of Classification Search ................ 514/47, 514/48, 51
See application file for complete search history.

(56) References Cited

U.S. PATENT DOCUMENTS

| | | | |
|---|---|---|---|
| 5,292,498 A | 3/1994 | Boucher, Jr. | 424/45 |
| 5,628,984 A | 5/1997 | Boucher, Jr. | 424/45 |
| 5,635,160 A | 6/1997 | Stutts, III et al. | 424/45 |
| 5,656,256 A | 8/1997 | Boucher et al. | 424/45 |
| 5,763,447 A | 6/1998 | Jacobus et al. | 514/265 |
| 5,789,391 A * | 8/1998 | Jacobus et al. | 514/51 |
| 5,837,861 A | 11/1998 | Pendergast et al. | 536/25.6 |
| 5,900,407 A | 5/1999 | Yerxa et al. | 514/47 |
| 5,902,567 A | 5/1999 | Boucher, Jr. | 424/9.1 |
| 5,935,555 A | 8/1999 | Stutts, III et al. | 424/45 |
| 5,958,897 A | 9/1999 | Jacobus et al. | 514/49 |
| 5,968,913 A | 10/1999 | LaCroix et al. | 514/47 |
| 5,972,904 A | 10/1999 | Jacobus et al. | 514/51 |
| 5,981,506 A | 11/1999 | Jacobus et al. | 514/47 |
| 6,022,527 A | 2/2000 | Boucher, Jr. et al. | 424/45 |
| 6,133,247 A | 10/2000 | Boucher, Jr. | 514/50 |
| 6,143,279 A | 11/2000 | Boucher, Jr. et al. | 424/45 |
| 6,147,056 A * | 11/2000 | Gilchrest et al. | 514/44 |
| 6,159,952 A * | 12/2000 | Shaffer et al. | 514/47 |
| 6,348,589 B1* | 2/2002 | Pendergast et al. | 536/25.6 |
| 6,610,274 B1* | 8/2003 | Gardner | 424/49 |
| 6,977,246 B2* | 12/2005 | Pendergast et al. | 514/47 |
| 2001/0026926 A1 | 10/2001 | Klein et al. | 33/569 |
| 2004/0241149 A1* | 12/2004 | De Simone | 424/93.45 |

FOREIGN PATENT DOCUMENTS

| | | |
|---|---|---|
| WO | WO94/08593 | 4/1994 |
| WO | WO96/40059 | 12/1996 |
| WO | WO97/05195 | 2/1997 |
| WO | WO97/29756 | 8/1997 |
| WO | WO97/35591 | 10/1997 |
| WO | WO98/03177 | 1/1998 |
| WO | WO98/15835 | 4/1998 |
| WO | WO98/03182 | 5/1998 |
| WO | WO98/19685 | 5/1998 |
| WO | WO98/34593 | 8/1998 |
| WO | WO 9834942 A2 * | 8/1998 |
| WO | WO99/09998 | 3/1999 |
| WO | WO 9909998 A1 * | 3/1999 |
| WO | WO99/32085 | 9/1999 |
| WO | WO99/61012 | 12/1999 |
| WO | WO98/34942 | 1/2000 |
| WO | WO00/30629 | 6/2000 |
| WO | WO00/50024 | 8/2000 |

OTHER PUBLICATIONS

Cury et al. Clinical Pharmacology of Agents Used in the Contemporary Management of Asthma. Jacksonville Medicine. Aug. 1998.*
Grrenberg et al. cAMP and Purinergic P2y Receptors Upragulate and Enhance Inducible NO Synthase mRNA and Protein in vivo. Am J Physiol Lung Cell Mol Physiol 273 (5): 967.*
Elgert, Klaus. Immunology. Wiley-Liss 1996. pp. 291-305.*
Goodman & Gilman's: The Pharmacological Basis of Therapeutics, 10th Edition, McGraw-Hill Medical Publishing Division, 2001, pp. 54-56.*
Brown, et al., "Evidence that UTP & ATP Regulate Phospholipase C through a Common Extracellular 5'-Nucleotide Receptor In Human Airway Epithelial Cells," *Mol. Pharmacol.* 40, 648-655 (1991).
Dichmann, et al., "Adenosine triphosphate-induced oxygen radical production and CD11b up-regulation: Ca++ mobilization and actin reorganization in human eosinophils," *Blood* 95(3): 973-8 (2000).
Ferrari, et al., "P2 purinergic receptors of human eosinophils: characterization and coupling to oxygen radical production," *FEBS Lett.* 486(3):217-24 (2000).

(Continued)

*Primary Examiner*—Shaojia Anna Jiang
*Assistant Examiner*—Traviss McIntosh
(74) *Attorney, Agent, or Firm*—Howrey LLP; Viola T. Kung (57) ABSTRACT

The present invention provides a method of preventing or treating an inflammatory disease, including but not limited to, sinusitis, rhinitis, conjunctivitis, asthma, dermatitis, inflammatory bowel disease, inflammatory collagen vascular diseases, glomerulonephritis, inflammatory skin diseases, and sarcoidosis. The method comprises administrating to a subject a pharmaceutical formulation comprising a nucleotide receptor agonist, such as nucleoside diphosphate, nucleoside triphosphate, or dinucleoside polyphosphate, according to general formula Ia, Ib, IIa, IIb, or III. Preferred indications of the present invention are perennial allergic rhinitis, seasonal allergic rhinitis, infectious allergic rhinitis, and allergic conjunctivitis.

18 Claims, 2 Drawing Sheets

OTHER PUBLICATIONS

Izushi et al., "Essential Role of ATP and Possibility of Activation of Protein Kinase C in $Ca^{2+}$—Dependent Histamine Release from Permeabilized Rat Peritoneal Mast Cells," *Pharmacology* 42(6): 297-308 (1991).

Jaffar et al., "Histamine secretion from mast cells stimulated with ATP," *Agents Actions* 30(1-2): 64-6 (1990).

Kannan, "Neutrophil degranulation: coactivation of chemokine receptor(s) is required for extracellular nucleotide-induced neutrophil degranulation," *Med. Hypotheses* 57(3): 306-9 (2001).

McCloskey, et al., "Chemotaxis of Rat Mast Cells Toward Adenine Nucleotides," *J. Immunol.* 163(2): 970-7 (1999).

Merritt et al., "Human Neutrophils Have a Novel Purinergic $P_2$-type Receptor Linked to Calcium Mobilization," *Cell Signal* 3(3): 243-9 (1991).

Mohanty, et al., "Effects of purine and pyrimidine nucleotides on intracellular $Ca^2 +$ in human eosinophils: Activation of purinergic P2Y receptors," *J. Allergy Clin. Immunol.* 107(5): 849-55 (2001).

Katzung, *Basic and Clinical Pharmacology* 431 (1989).

Saito, et al., "Extracellular ATP Stimulates Interleukin-Dependent Cultured Mast Cells and Eosinophils through Calcium Mobilization," *Int. Arch. Allergy Appl. Immunol.* 94(1-4): 68-70 (1991).

Schulman, et al., "ATP Modulates Anti-IgE-Induced Release of Histamine from Human Lung Mast Cells," *Am. J. Respir. Cell. Mol. Biol.* 20(3): 530-7 (1999).

Walker, et al., "Nucleotide Responses of Human Neutrophils," *Lab Invest.* 64(1): 105-12 (1991).

Yerxa, et al., "$P2Y_2$ receptor agonists: structure, activity and therapeutic utility," *Drugs of the Future* 24(7): 759-769 (1999).

http://www.graylab.ac.uk/cgi.bin/omd?query=allegy, Oct. 19, 2001.

http://www.medterms.com/script/main/ad/asp?articlekey=3979, Oct. 23, 2001.

International Search Report dated Feb. 20, 2003.

Greenberg, et al., "cAMP and purinergic P2y receptors upregulate and enhance inducible NO synthase mRNA and protein in vivo," The American Physiological Society pp. L967-L977, 1997.

Loredo & Benton, "ATP and UTP Activate Calcium-Mobilizing $P_{2u}$-like Receptors and Act Synergistically with Interleukin-1 to Stimulate Prostaglandin $E_2$ Release from Human Rheumatoid Synovial Cells," *Arthritis & Rheumatism* 41:2 pp. 246-255 (1998).

\* cited by examiner

METHOD FOR TREATING OR PREVENTING INFLAMMATORY DISEASES

This application claims the benefit of U.S. Provisional Application No. 60/337,828, filed Nov. 6, 2001.

TECHNICAL FIELD

This invention relates to a method of treating, preventing and/or alleviating the symptoms and manifestations of inflammatory diseases. This invention also relates to a method of treating, preventing, and/or alleviating the symptoms and manifestation of allergic reactions. Nucleotide receptor agonists are used in the present invention.

BACKGROUND OF THE INVENTION

Studies suggest that activation of P2Y receptors and/or P2X receptors by extracellular nucleotides (such as ATP and UTP) elicit responses from inflammatory cells (such as mast cells, eosinophil, leukocytes, neutrophils) consistent with a pro-inflammatory effect. ATP is required to stimulate histamine release from rat peritoneal mast cells and histamine and prostaglandin D2 in rat serosal mast cells (Jaffar and Pearce, *Agents Actions* 30(1-2): 64-6 (1990); Izushi and Tasaka, *Pharmacology* 42(6): 297-308 (1991)). In the latter case, the effects of ATP were inhibited by reactive blue 2 and suramin, two putative antagonists for P2Y receptors. Anti-IgE-induced histamine release from human lung mast cells was significantly enhanced by ATP and UTP at low concentrations ($10^{-6}$ to $10^{-4}$ M) but inhibited at high concentrations ($10^{-3}$ M), indicating a bimodal action (Schulman, et al., *Am. J. Respir. Cell. Mol. Biol.* 20(3):530-7(1999)). Adenine and uridine nucleotides (ADP, ATP, and UTP) activate chemotaxic signals on cultured rat bone marrow mast cells and may function to recruit mast cells by intestinal mucosa as part of a parasitic response (Saito, et al., *Int. Arch. Allergy Appl. Immunol.* 94(1-4): 68-70 (1991); McCloskey, et al., *J. Immunol.* 163(2): 970-7 (1999)).

Purinergic receptors, via the action of ATP and UTP, were also shown to be involved in nucleotide responses of human neutrophils in mediating an enhanced $O_2$ response to the chemotactic peptide N'-formyl-Met-Leu-Phe (Walker, et al., *Lab Invest.* 64(1): 105-12 (1991)). For example, short incubations of polymorphonuclear leukocyte (PMN) with ATP and UTP enhanced the oxidative burst induced by N'-formyl-Met-Leu-Phe. In human neutrophils, ATP was shown to stimulate the elevation of cytosolic free calcium concentration via the action of a P2 receptor (Merritt and Moores, *Cell Signal* 3(3):243-9 (1991); Walker, et al., *Lab Invest.* 64(1): 105-12.et al. (1991)).

Extracellular nucleotide-induced stimulation of leukocytes and subsequent adhesion to endothelium has been shown to play an important role in inflammatory diseases. Extracellular nucleotides stimulate P2Y receptor on human polymorphonuclear neutrophils (PMN) with the pharmacological profile of the $P2Y_2$ receptor. It is postulated that extracellular nucleotides require leukotriene generation as an essential intermediate for mediating neutrophil degranulation (Kannan, *Med. Hypotheses* 57(3): 306-9 (2001)).

Extracellular nucleotides also elicit multiple responses in eosinophils, which have been shown to express various P2X and P2Y subtypes (Ferrari, et al., *FEBS Lett.* 486(3): 217-24 (2000)). For example, ATP was shown in human eosinophils to stimulate cytosolic calcium levels, production of reactive oxygen species, and upregulation of the pro-inflammatory marker integrin CD11b (Dichmann, et al., *Blood* 95(3): 973-8 (2000)). In addition to such actions, P2Y agonists have also been shown to increase intracellular $Ca^{++}$ due to stimulation of phospholipase C by the $P2Y_2$ receptor (Brown, et al., *Mol. Pharmacol.* 40, 648-655 (1991); Yerxa and Johnson, *Drugs of the Future* 24(7): 759-769 (1999)). ATP is a strong activator of eosinophils, with biological activity comparable to those of other known neutrophilic chemotaxins, thereby strongly suggesting a role of P2 receptors as activators of pro-inflammatory effector functions (Dichmann, et al., *Blood* 95(3): 973-8 (2000); Mohanty, et al., *J. Allergy Clin. Immunol.* 107(5): 849-55 (2001)).

The preponderance of observations suggests that activation of P2Y receptors and/or P2X receptors by extracellular nucleotides such as ATP and UTP elicit responses from inflammatory cells (such as mast cells, eosinophil, leukocytes, neutrophils) consistent with a pro-inflammatory effect. Thus these findings suggest a role of P2Y receptor agonists in increasing inflammatory effects.

Purinergic receptor agonists have been disclosed in the following patents. U.S. Pat. Nos. 5,789,391; 5,763,447; 5,635,160; 5,935,555; 5,656,256; 5,628,984; 5,902,567; 5,292,498; 5,837,861; 5,900,407; 5,972,904; 5,981,506; 5,958,897; 5,968,913; 6,022,527; 6,133,247; and 6,143,279, and PCT publications WO97/29756, WO97/35591, WO96/40059, WO97/05195, WO94/08593, WO98/19685, WO98/15835, WO98/03182, WO98/03177, WO98/34942, WO98/34593, WO99/09998, WO99/32085, WO99/61012, WO 00/30629, WO 00/50024, and WO 96/40059 disclose methods of treating sinusitis, otitis media, ciliary dyskinesia, pneumonia associated with immobilization, lung disease, cystic fibrosis, dry eye disease, vaginal dryness, bronchitis, edematous retinal disorders, retinal degeneration and detachment, and gastrointestinal disease, by administrating dinucleoside polyphosphates and related compounds to a patient.

The search for compounds that counteract or inhibit inflammatory effects is still an area of active research. It would be very desirable to find new compounds with this ability, particularly if these compounds were to function via unknown pathways.

SUMMARY OF THE INVENTION

The present invention provides a method of preventing or treating inflammatory diseases. The method comprises administering to a subject in need thereof a pharmaceutical formulation comprising a nucleotide receptor agonist in an amount effective to treat or prevent inflammatory diseases.

Nucleotide receptor agonists are preferably P2Y receptor agonists and include nucleoside diphosphates, nucleoside triphosphates, dinucleoside polyphosphates and their analogs. Nucleoside diphosphates useful in this application include for example uridine 5'-diphosphate (UDP), adenosine 5'-diphosphate (ADP), cytidine 5'-diphosphate (CDP) and their analogs of general Formulae Ia and Ib. Nucleoside triphosphates useful in this application include for example uridine 5'-triphosphate (UTP), adenosine 5'-triphosphate (ATP), cytidine 5'-triphosphate (CTP) and their analogs of general Formulae IIa and IIb. Dinucleoside polyphosphates useful in this application are described as general Formula III.

Inflammatory diseases suitable for prevention or treatment by this invention include, but are not limited to, sinusitis, rhinitis, conjunctivitis, asthma, dermatitis, inflammatory bowel disease, inflammatory collagen vascular diseases, glomerulonephritis, inflammatory skin diseases, and sarcoidosis. The most common causes of inflammatory

DETAILED DESCRIPTION OF THE INVENTION

Applicants have unexpectedly discovered that, contrary to previous teachings, P2Y receptor agonists can counteract or inhibit inflammatory effects. Applicants have discovered that the activation of P2Y receptors in vivo provides a receptor pathway for treating, preventing, and/or alleviating pro-inflammatory effects, and thereby provide a method of preventing or treating inflammatory diseases. This notion is clearly taught away from in the prior art.

Most of the biological systems used to investigate the effects of P2Y activation on inflammatory cells were conducted in vitro, and Applicants thought that results from such systems may have provided an incomplete view of the roles of P2Y receptors in inflammatory and allergic conditions. Applicants decided to independently investigate, and have since shown in two in vivo models of allergic conjunctivitis that a P2Y receptor agonist, $UP_4U$, reduced the pro-inflammatory markers of the allergic reactions associated with allergic conjunctivitis. Applicants have also shown that $UP_4dC$ enhances mucociliary clearance of nasal tissue in humans. Applicants have further shown that $UP_4dC$ nasal spray is effective in reducing the symptoms of perennial allergic rhinitis in humans.

The present invention provides a method for treating or preventing inflammatory diseases using an agonist of nucleotide receptors. Nucleotide receptors are membrane-bound proteins that selectively bind extracellular nucleotides, such as UTP and ATP. Preferred nucleotide receptors are P2Y purinergic receptors such as $P2Y_2$ receptors. The present invention features a method of alleviating or reversing the symptoms of an inflammatory disease.

The method comprises administering to a subject in need thereof a pharmaceutical formulation comprising an effective amount of a nucleotide receptor agonist or pharmaceutically acceptable salts thereof, optionally with a pharmaceutically suitable carrier. An effective amount is an amount effective to prevent or treat an inflammatory disease; an effective amount can be determined by various known techniques performed by those skilled in the art.

Inflammation occurs when immunologically competent cells are activated in response to foreign organisms or antigenic proteins. The inflammatory process can be either beneficial, as when it causes invading organisms to be phagocytosed or neutralized, but it also can be deleterious, as in the case of arthritis, when it leads to the destruction of bone and cartilage and the resulting limitation of joint function. The inflammatory response is usually triggered by trauma or antigens, such as viral, bacterial, protozoal, or fungal antigens. The cell damage associated with inflammation acts on cell membranes to cause leukocytes to release lysosomal enzymes. Arachidonic acid is then released from precursor compounds and various eicosanoids are produced. Leukotrienes have a powerful chemotactic effect on eosinophils, neutrophils and macrophages, thereby promoting bronchoconstriction and changes in vascular permeability. Kinins, neuropeptides, histamine, complement components, and other products of leukocytes and platelets are released at the site of tissue injury. Stimulation of the neutrophil membrane produces oxygen-derived free radicals, such as superoxide anion, which in turn stimulates the production of other reactive molecules, such as hydrogen peroxide and hydroxyl radicals. The interaction of these substances with arachidonic acid results in the production of chemotactic substances, thereby perpetuating the inflammatory process (Payan, D. G. and Shearn, M. A., pp. 431, in *Basic and Clinical Pharmacology*, Ed. Katzung, Bertram G., Appleton and Lange, East Norwalk, Conn., 1989).

Inflammatory diseases suitable for prevention or treatment by the present invention include, but are not limited to, sinusitis, rhinitis, conjunctivitis, asthma, dermatitis, inflammatory bowel disease, inflammatory collagen vascular diseases, glomerulonephritis, inflammatory skin diseases, and sarcoidosis. For certain diseases, the root cause of the inflammation can be varied and include those induced from infection, allergy, and non-allergy. For example, rhinitis-type inflammation includes rhinitis induced from infection, allergic rhinitis, and non-allergic rhinitis (drug-induced, mechanical and gustatory). The most common causes of inflammatory diseases are allergies and infections; the allergy or infection caused inflammatory diseases are particularly suitable for the prevention or treatment by this invention.

Upper respiratory infection (in nose, sinuses, and pharynx), a leading cause of inflammation, also referred to as the common cold, causes inflammation that is associated with sinusitis and rhinitis.

Atopic dermatitis, also known as atopic eczema/dermatitis syndrome, is an inflammatory skin disease suitable for the present invention. In atopic dermatitis, an aggregation of several allergic and nonallergic mechanisms causes the surface of the skin to swell and flake off; such inflammation produces symptoms such as rash, itching, burning, stinging, and pain.

Allergy is a state of hypersensitivity caused by exposure to a specific antigen (allergen) resulting in harmful immunologic reactions or subsequent exposures. Allergy usually refers to hypersensitivity to an environmental antigen (atopic allergy or contact dermatitis) or to a drug allergy (http://www.graylab.ac.uk/cgi-bin/omd?query=allergy, Oct. 19, 2001). The first encounter with an allergen sensitizes the body via the lymphocytes, resulting in IgE coating of mast cells and basophils. Subsequent exposure results in the development of the "early phase" of the allergic reaction and occurs within seconds or minutes of exposure to an allergen. The early phase is also known as the immediate hypersensitivity reaction. In an allergic reaction, hypersensitivity is a condition in a previously exposed person, in which tissue inflammation is caused by an immune reaction upon re-exposure to an allergen sensitizer. In half of occurrences, the allergic reaction develops into a "late phase," which occurs about 4 to 6 hours after the exposure. In the late phase reaction, tissues become red and swollen due to the collection of eosinophils, neutrophils, lymphocytes, and other cells. Cytokines released by mast cells and basophils signal such other cells to the area of inflammation. Additional cytokines are released by TH₂ lymphocytes and further attract cells of inflammation. Eosinophils, which are often numerous in the blood of people with allergies, collect at the site of allergic reaction, release chemicals that cause damage to tissues, and continue to promote inflammation. Repeated episodes of this "late phase" reaction contribute to chronic allergic symptoms, sensitizing the tissues to subsequent exposure. Examples of allergic reactions include pulmonary (eg. asthma), nasal (eg. rhinitis), cutaneous, ocular (eg. conjunctivitis), and systemic late phase reactions (http://www.medterms.com/script/main/art.asp?articlekey=3979, Oct. 23, 2001).

Allergy suitable for prevention or treatment by the present invention includes, but not limited to, asthma, allergic rhinitis, allergic dermatitis, and allergic conjunctivitis.

Allergic rhinitis is an inflammatory state characterized by numerous symptoms such as nasal congestion, nasal discharge, post-nasal drip, sore throat, sneezing, headache, itching of the nose and throat, facial pressure and pain, and general malaise. Allergic rhinitis can generally be classified as perennial, seasonal, occupational, hormonal, infectious, and idiopathic.

Perennial allergic rhinitis (PAR) is the most common type of allergic rhinitis, and is typically caused by exposure to allergens such as mold spores, dust mites, animal dander and others, and can occur at any time of year. This is generally viewed as a chronic disease. Seasonal allergic rhinitis, also known as hay fever, is a reaction to pollen or mold and typically occurs during certain seasons, for example during "rag weed season" in certain locals. The duration of the allergic reactions can be several days to a few months. Occupational allergic rhinitis is similar to PAR, but it is triggered by a response to airborne allergens at work. Infectious allergic rhinitis occurs during an upper respiratory infection, such as during the common cold, in which the infecting organism releases inflammatory mediators that trigger an allergic response. Symptoms last throughout the time of infection and are often associated with an increase in sinus and bronchial infections. Hormonal allergic rhinitis occurs typically during pregnancy or in patients with other hormonal imbalances such as hypothyroidism. Idiopathic allergic rhinitis is a term used to describe allergic rhinitis in which either the allergen is not known or the cause of the inflammatory rhinitis symptoms is best defined as perennial nonallergic.

Allergic conjunctivitis is often associated with allergic rhinitis symptoms and has additional ocular symptoms such as itchy, watery, burning, stinging, scratchy and red eyes, headache and light sensitivity. Allergic conjunctivitis includes atopic keratoconjunctivitis and vernal conjunctivitis. Atopic keratoconjunctivitis is an allergic ocular disease characterized by itching, burning, tearing, photophobia and pain and often associated with blepharitis and meibomianitis (inflammation of eyelids).

Preferred indications of the present invention are perennial allergic rhinitis, seasonal allergic rhinitis, infectious allergic rhinitis, and allergic conjunctivitis.

Description of Compounds

The present method comprises administering to a subject in need thereof a pharmaceutical formulation comprising an effective amount of a nucleotide receptor agonist. Preferred nucleotide receptors are P2Y purinergic receptors, such as the P2Y₂ receptors. Activation of such receptors by P2Y agonists trigger the elevation of intracellular calcium levels and activation of signaling pathways, thus leading to prevention or treatment of an inflammatory disease.

Nucleotide receptor agonists include nucleoside polyphosphates, dinucleoside polyphosphates and their analogs. Nucleoside diphosphates useful in this application include uridine 5'-diphosphate (UDP), adenosine 5'-diphosphate (ADP), cytidine 5'-diphosphate (CDP) and their analogs of general Formulae Ia and Ib. Nucleoside triphosphates useful in this application include uridine 5'-triphosphate (UTP), adenosine 5'-triphosphate (ATP), cytidine 5'-triphosphate (CTP) and their analogs of general Formulae IIa and IIb; dinucleoside polyphosphates of general Formula III are also useful in this application.

UDP, CDP and their analogs are depicted by general Formula Ia:

Formula Ia wherein:
  $X_1$ and $X_2$ are each independently OH, SH, O⁻ or S⁻;
  Y is H or OH;
  $R_1$ is O, imido, methylene, or dihalomethylene;
  $R_2$ is H, halogen, aryl, alkyl, substituted aryl, substituted alkyl, alkenyl, alkynyl, arylalkyl, arylalkenyl, arylalkynyl, alkoxy, nitro, or azido;
  $R_3$ is H, alkyl, acetyl, benzoyl, acyl, arylacyl, arylalkyl, or is absent when there is a double bond between N-3 and C-4; and
  $R_4$ is —OR', —SR', NHR", or NR'R", wherein R' is H, alkyl, substituted alkyl, aryl, substituted aryl, or arylalkyl; and R" is H, alkyl, substituted alkyl, aryl, substituted aryl, arylalkyl alkoxy, or aryloxy; provided that when $R_4$ is double bonded to the carbon at the 4-position of the pyrimidine ring, R' is absent; or R" is absent, and R' of NR'R" and $R_3$ taken together are —CH=CH— forming a ring from N-3 to N-4 with a double bond between N-4 and C-4; optionally, the hydrogens of the 4- or 5-position of the etheno ring are independently substituted with alkyl, substituted alkyl, aryl, substituted aryl, alkoxy, nitro, halo, or azido.

Formula Ia compounds, for example, include: uridine 5'-diphosphate (UDP); uridine 5'-O-(2-thiodiphosphate) (UDPβS); 5-bromouridine 5'-diphosphate (5-BrUDP); 5-(1-phenylethynyl)-uridine 5'-diphosphate(5-(1-phenylethynyl)UDP); 5-methyluridine 5'-diphosphate (5-methylUDP); 4-hexylthiouridine 5'-diphosphate (4-hexylthioUDP); 4-mercaptouridine 5'-diphosphate (4-mercaptoUDP); 4-methoxyuridine 5'-diphosphate (4-methoxyUDP); 4-(N-morpholino)uridine 5'-diphosphate (4-(N-morpholino)UDP); 4-hexyloxyuridine 5'-diphosphate (4-hexyloxyUDP); N,N-dimethylcytidine 5'-diphosphate (N,N-dimethylCDP); N-hexylcytidine 5'-diphosphate (N-hexylCDP); and N-cyclopentylcytidine 5'-diphosphate (N-cyclopentylCDP).

Preferred compounds of Formula Ia include UDP and UDPβS and 4-thio UDP. Certain compounds of Formula Ia (e.g., UDP, dUDP, UDPβS, and 4-mercaptoUDP) are known and may be made in accordance with known procedures or variations thereof, which will be apparent to those skilled in the art. For example, the identification and preparation of certain thiophosphate analogs of nucleoside diphosphates (such as UTP-β-S) are set forth in U.S. Pat. No. 3,846,402 and Goody and Eckstein (*J. Am. Chem. Soc.* 93: 6252-6257 (1971)). Alternatively, UDP, and other analogs thereof are also commercially available from vendors such as Sigma (St. Louis, Mo.) and Pharmacia (Uppsala, Sweden).

ADP and its analogs are depicted by general Formula Ib:

Formula Ib wherein:

$R_1$, $X_1$, $X_2$ and Y are defined as in Formula Ia;

$R_{11}$ is hydrogen, chlorine, amino, monosubstituted amino, disubstituted amino, alkylthio, arylthio, or aralkylthio, wherein the substituent on sulfur contains up to a maximum of 10 carbon atoms, with or without unsaturation;

$R_{12}$ is hydroxy, alkenyl, oxo, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, or diacylamino;

$R_X$ is O, H, or is absent;

$R_{12}$ and $R_X$ are optionally taken together to form a 5-membered fused imidazole ring of 1, $N^6$-ethenoadenine derivatives, optionally substituted on the 4- or 5- positions of the etheno moiety with alkyl, aryl, nitroaryl, haloaryl, aralkyl, or alkoxy moieties as defined below;

$R_{13}$ is hydrogen, azido, alkoxy, aryloxy, aralkyloxy, alkylthio, arylthio, or aralkylthio as defined below; or $T(C_{1-6}$alkyl)OCONH($C_{1-6}$alkyl)W—wherein T and W are independently amino, mercapto, hydroxy, or carboxyl; or pharmaceutically acceptable esters, amides or salts thereof;

J is carbon or nitrogen, with the provision that when J is nitrogen, $R_{13}$ is not present;

wherein the alkyls are straight-chain, branched or cyclic;

wherein the aryl groups are optionally substituted with lower alkyl, aryl, amino, mono- or dialkylamino, $NO_2$, $N_3$, cyano, carboxylic, amido, sulfonamido, sulphonic acid, phosphate, or halo groups;

Particularly preferred compounds of Formula Ib include 5'-adenosine diphosphate (ADP) and 2-methyl-SADP.

UTP, CTP and their analogs are depicted by general Formula IIa;

Formula IIa wherein:

$X_1$, $X_2$ and $X_3$ are each independently either OH, SH, $O^-$ or $S^-$;

Y is H or OH;

$R_1$, $R_2$, $R_3$ and $R_4$ are defined as in Formula Ia.

Preferably, $X_2$ and $X_3$ are $O^-$, $R_1$ is oxygen or imido, and $R_2$ is H. Particularly preferred compounds of Formula IIa include uridine 5'-triphosphate (UTP) and uridine 5'-O-(3-thiotriphosphate) (UTPγS), cytidine 5'-triphosphate (CTP) and 4-nitrophenyl ethenocytidine 5'-triphosphate.

ATP and its analogs are depicted by general Formula IIb:

Formula IIb wherein:

$R_1$, $X_1$, $X_2$, $X_3$ and Y are defined as in Formula IIa;

wherein:

$R_{11}$ is hydrogen, chlorine, amino, monosubstituted amino, disubstituted amino, alkylthio, arylthio, or aralkylthio, wherein the substituent on sulfur contains up to a maximum of 10 carbon atoms, with or without unsaturation;

$R_{12}$ is hydroxy, alkenyl, oxo, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, or diacylamino;

$R_X$ is O, H, or is absent;

$R_{12}$ and $R_X$ are optionally taken together to form a 5-membered fused imidazole ring of 1, $N^6$-ethenoadenine derivatives, optionally substituted on the 4- or 5- positions of the etheno moiety with alkyl, aryl or aralkyl moieties as defined below;

$R_{13}$ is hydrogen, azido, alkoxy, aryloxy, aralkyloxy, alkylthio, arylthio, or aralkylthio as defined below; or $T(C_{1-6}$alkyl)OCONH($C_{1-6}$alkyl)W—wherein T and W are independently amino, mercapto, hydroxy, or carboxyl; or pharmaceutically acceptable esters, amides or salts

J is carbon or nitrogen, with the provision that when J is nitrogen, $R_{13}$ is not present;

wherein the alkyls are straight-chain, branched or cyclic; and wherein the aryl groups are optionally substituted with lower alkyl, aryl, amino, mono- or dialkylamino, $NO_2$, $N_3$, cyano, carboxylic, amido, sulfonamido, sulphonic acid, phosphate, or halo groups.

Dinucleoside polyphosphates are depicted by general Formula III:

Formula III wherein:
O⁻ can be OH or a salt form,
X is oxygen, methylene, dihalomethylene (with difluoromethylene and dichloromethylene preferred), or imido;
n=0, 1 or 2;
m=0, 1 or 2;
n+m=0,1,2,3 or 4;
Z=H or OH;
Z'=H or OH;
Y=H or OH;
Y'=H or OH; and
wherein at least one of Z, Z', Y, or Y' is OH; and
B and B' are each independently a purine residue or a pyrimidine residue, as defined in Formula IIIa and IIIb, respectively, linked through the 9- or 1-position, respectively;

Formula IIIa wherein:
$R_{11}$ is hydrogen, chlorine, amino, monosubstituted amino, disubstituted amino, alkylthio, arylthio, or aralkylthio, wherein the substituent on sulfur contains up to a maximum of 10 carbon atoms, with or without unsaturation;

$R_{12}$ is hydroxy, alkenyl, oxo, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, or diacylamino;

$R_X$ is O, H, or is absent;

$R_{12}$ and $R_X$ are optionally taken together to form a 5-membered fused imidazole ring of 1, $N^6$-ethenoadenine derivatives, optionally substituted on the 4- or 5-positions of the etheno moiety with alkyl, aryl or aralkyl moieties as defined below;

$R_{13}$ is hydrogen, azido, alkoxy, aryloxy, aralkyloxy, alkylthio, arylthio, or aralkylthio as defined below; or $T(C_{1-6}$alkyl)OCONH$(C_{1-6}$alkyl)W—wherein T and W are independently amino, mercapto, hydroxy, or carboxyl; or pharmaceutically acceptable esters, amides or salts thereof;

J is carbon or nitrogen, with the provision that when J is nitrogen, $R_{13}$ is not present;

wherein the alkyls are straight-chain, branched or cyclic;

wherein the aryl groups are optionally substituted with lower alkyl, aryl, amino, mono- or dialkylamino, $NO_2$, $N_3$, cyano, carboxylic, amido, sulfonamido, sulphonic acid, phosphate, or halo groups;

Formula IIIb wherein:
$R_{14}$ is hydroxy, oxo, mercapto, thione, amino, cyano, $C_{7-12}$arylalkoxy, $C_{1-6}$ alkylthio, $C_{1-6}$alkoxy, $C_{1-6}$ alkylamino, or di$C_{1-4}$alkylamino, wherein the alkyl groups are optionally linked to form a heterocycle;

$R_{15}$ is hydrogen, acetyl, benzoyl, alkyl, alkanoyl, aroyl, acyl, arylacyl, or is absent when there is a double bond between N-3 and C-4;

$R_{16}$ is hydroxy, oxo, mercapto, thione, $C_{1-4}$alkoxy, $C_{7-12}$arylalkoxy, $C_{1-6}$alkylthio, S-phenyl, arylthio, aralkylthio triazolyl, amino, $C_{1-6}$alkylamino, $C_{1-5}$ disubstituted amino, or di-$C_{1-4}$alkylamino, wherein said dialkyl groups are optionally linked to form a heterocycle or linked to form a substituted ring, such as morpholino, pyrrolo, etc.; or $R_{15}$ and $R_{16}$ taken together form a 5-membered fused imidazole ring between positions 3 and 4 of the pyrimidine ring and form a 3, $N^4$-ethenocytosine derivative, wherein said etheno moiety is optionally substituted on the 4- or 5-positions with $C_{1-4}$ alkyl, phenyl or arylalkyl, wherein at least one hydrogen of said $C_{1-4}$ alkyl, phenyl or arylalkyl is optionally substituted with halogen, hydroxy, $C_{1-4}$alkoxy, $C_{1-4}$alkyl, $C_{6-10}$aryl, $C_{7-12}$arylalkyl, carboxy, cyano, sulfonamido, sulfonate, phosphate, sulfonic acid, amino, $C_{1-4}$ alkylamino, and di-$C_{1-4}$alkylamino, wherein said dialkyl groups are optionally linked to form a heterocycle;

$R_{17}$ is hydrogen, hydroxy, cyano, nitro, halogen, $C_{1-6}$alkyl, $C_{2-8}$alkenyl, $CF_3$, phenyl, $C_{2-8}$alkynyl, allylamino, bromovinyl, ethyl propenoate, or propenoic acid; or $R_{16}$ and $R_{17}$ together form a 5 or 6-membered saturated or unsaturated ring bonded through N or O or S at $R_{16}$, such ring optionally contains substituents that themselves contain functionalities; and $R_{18}$ is hydrogen, amino, alkylamino, acylamino, di-$C_{1-4}$ alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, or phenylthio; provided that when $R_{18}$ is amino or substituted amino, $R_{17}$ is hydrogen.

As used herein, the term "alkyl" refers to $C_{1-10}$ inclusive, linear, branched, or cyclic, saturated or unsaturated (i.e., alkenyl and alkynyl) hydrocarbon chains, for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, allenyl and optionally substituted arylalkenyl and arylalkynyl groups. As used herein, the term "acyl" refers to an organic acid group wherein the —OH of the carboxyl group has been replaced with another substituent (i.e., as represented by RCO—, wherein R is an alkyl or an aryl group). As such, the term "acyl" specifically includes arylacyl groups. Specific examples of acyl groups include acetyl and benzoyl. As used herein, the term "aryl" refers to 5 and 6-membered hydrocarbon and heterocyclic aromatic rings. Examples of aryl groups include cyclopentadienyl, phenyl, furan, thiophene, pyrrole, pyran, pyridine, imidazole, isothiazole, isoxazole, pyrazole, pyrazine, pyrimidine group, and the like. The term "alkoxy" as used herein refers to $C_{1-10}$ inclusive, linear, branched, or cyclic, saturated or unsaturated hydrocarbon chains bound through an oxygen group, including for example methoxy, ethoxy, propoxy, isopropoxy, butoxy, t-butoxy, and pentoxy. The term "aryloxy" as used herein refers to aryloxy such as phenyloxy, and alkyl, halo, or alkoxy group, substituted aryloxy. As used herein, the terms "substituted alkyl" and "substituted aryl" include alkyl and aryl groups, as defined herein, in which one or more atoms or functional groups of the aryl or alkyl group are replaced with another atom or functional group, for example, halogen, aryl, alkyl, alkoxy, hydroxy, nitro, amino, alkylamino, dialkylamino, sulfonyl, or mercapto. The terms "halo," "halide," or "halogen" as used herein refer to fluoro, chloro, bromo, or iodo groups.

The furanosyl moieties of Formulae Ia, Ib, IIa, IIb and III are as depicted in the D-configuration, but may be L-, or D- and L-. The D-configuration is preferred. The nucleoside residue can be an alpha- or beta- and D- or L-configurations, but most preferably the beta-D-configuration. The furanosyl moieties include ribofuranosyl, 2'-deoxyribofuranosyl, 3'-deoxyribofuranosyl, 2',3'-dideoxyribofuranosyl, arabinofuranosyl, 3'-deoxyarabinofuranosyl, xylofuranosyl, 2'-deoxyxylofuranosyl, and lyxofuranosyl.

In the general structure of Formulae Ib, IIb, and IIIa, the dotted lines are intended to indicate the presence of single or double bonds in these positions; the relative positions of the double or single bonds being determined by whether the $R_{12}$ and $R_X$ substituents are capable of keto-enol tautomerism.

In the general structure of Formulae Ia and IIa, the dotted lines in the 4- to 5-positions are intended to indicate the presence of single or double bonds in these positions; the relative positions of the double or single bonds being determined by whether the $R_3$ and $R_4$ substituents are capable of keto-enol tautomerism.

In the general structure of Formulae IIIb, the dotted lines in the 2- to 6-positions are intended to indicate the presence of single or double bonds in these positions; the relative positions of the double or single bonds being determined by whether the $R_{14}$, $R_{15}$, $R_{16}$, $R_{17}$, and $R_{18}$ substituents are capable of keto-enol tautomerism.

In the general structures of Formulae Ia, Ib, IIa, IIb, III, IIIa, and IIIb, above, the acyl groups comprise alkanoyl or aroyl groups. The alkyl groups contain 1 to 8 carbon atoms, particularly 1 to 4 carbon atoms optionally substituted by one or more appropriate substituents, as described below. The aryl groups are preferably phenyl groups, and are optionally substituted by one or more appropriate substituents, as described below. The above-mentioned alkenyl and alkynyl groups contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are selected from halogen, hydroxy, $C_{1-4}$alkoxy, $C_{1-4}$alkyl, $C_{6-12}$aryl, $C_{6-12}$arylalkoxy, carboxy, cyano, nitro, sulfonamido, sulfonate, phosphate, sulfonic acid, amino and substituted amino wherein the amino is singly or doubly substituted by a $C_{1-4}$alkyl, and when doubly substituted, the alkyl groups optionally being linked to form a heterocycle.

Substituted derivatives of adenine moiety include adenine 1-oxide; 1, $N^6$-(4- or 5-substituted etheno) adenine; $N^6$-substituted adenine; or N-substituted 8-aminoadenine, wherein said substituted groups are chosen from among: arylalkyl ($C_{1-6}$) groups with the aryl moiety optionally functionalized as described below: alkyl; and alkyl groups with functional groups therein, such as: ([6-aminohexyl]carbamoylmethyl)-, ω-acylated-amino(hydroxy, thiol and carboxy)alkyl ($C_{2-10}$)— and their ω-acylated-amino (hydroxy, thiol and carboxy) derivatives wherein the acyl group is chosen from among, but not limited to, acetyl, trifluoroacetyl, benzoyl, substituted-benzoyl, etc., or the carboxylic moiety is present as its ester or amide derivative, for example, the ethyl or methyl ester or its methyl, ethyl or benzamido derivative. The ω-amino(hydroxy, thiol) moiety may be alkylated with a $C_{1-4}$alkyl group.

Dinucleoside polyphosphates of general Formula III include dinucleoside tetraphosphates selected from the group consisting of $P^1,P^4$-di(uridine 5'-)tetraphosphate; $P^1$-(cytidine 5')-$P^4$-(uridine 5'-)tetraphosphate; $P^1,P^4$-di(adenosine 5'-)tetraphosphate; $P^1$-(adenosine 5')-$P^4$-(uridine 5'-)tetraphosphate; $P^1$-(adenosine 5')-$P^4$-(cytidine 5'-)tetraphosphate; $P^1,P^4$-di(ethenoadenosine)tetraphosphate; $P^1$-(uridine 5')-$P^4$-(thymidine 5'-)tetraphosphate; $P^1$-(adenosine 5')-$P^4$-(inosine 5'-)tetraphosphate; $P^1,P^4$-di(uridine 5')-$P^2$,$P^3$-methylenetetraphosphate; $P^1,P^4$-di(uridine 5')-$P^2$,$P^3$-difluoromethylenetetraphosphate; $P^1,P^4$-di(uridine 5')-$P^2$,$P^3$-imidotetraphosphate; $P^1,P^4$-di(4-thiouridine 5'-)tetraphosphate; $P^1,P^5$-di(uridine 5'-)pentaphosphate; $P^1,P^4$-di(3, $N^4$-ethenocytidine 5'-)tetraphosphate; $P^1,P^4$-di(imidazo[1,2-c]pyrimidine-5(6H)-one-2-(3-nitro)-phenyl-6-β-D-ribofuranoside 5'-)tetraphosphate; $P^1$-(inosine 5')-$P^4$-(uridine 5'-)tetraphosphate; $P^1$-(cytosineβ-D-arabinofuranoside 5')-$P^4$-(uridine 5'-)tetraphosphate; $P^1$-(uridine 5')-$P^4$-(xanthosine 5'-)tetraphosphate; $P^1$-(2'-deoxyuridine 5')-$P^4$-(uridine 5'-)tetraphosphate; $P^1$-(3'-azido-3'-deoxythymidine 5)-$P^4$-(uridine 5'-)tetraphosphate; $P^1,P^4$-di(3'-azido-3'-deoxythymidine 5'-)tetraphosphate; 2'(3')-benzoyl-$P^1,P^4$-di(uridine 5'-)tetraphosphate; $P^1,P^4$-di[2',(3')-benzoyluridine 5'-]tetraphosphate; $P^1$-(2'-deoxyguanosine 5')-$P^4$-(uridine 5'-)tetraphosphate; $P^1$-(2-'-deoxyadenosine 5')-$P^4$-(uridine 5'-)tetraphosphate; $P^1$-(2'-deoxyinosine 5')-$P^4$-(uridine 5'-)tetraphosphate; $P^1$-(2'-deoxycytidine 5')-$P^4$-(uridine 5'-)tetraphosphate; $P^1$-(4-thiouridine 5')-$P^4$-(uridine 5'-)tetra-phosphate; $P^1$-(8-azaadenosine 5')-$P^4$-(uridine 5'-)tetraphosphate; $P^1$-(6-mercaptopurine riboside 5')-$P^4$-(uridine 5'-)tetraphosphate; $P^1$-(6-mercaptopurine riboside 5')-$P^4$-(2'-deoxyuridine 5'-)tetraphosphate; $P^1$-(4-thiouridine 5')-$P^4$-(cytosine-β-D-arabinofuranoside 5'-)tetraphosphate; $P^1$-(adenosine 5')-$P^4$-(4-thiomethyluridine 5'-)tetraphosphate; $P^1$-(2'-deoxyadenosine 5')-$P^4$-(6-thiohexylpurine riboside 5'-)tetraphosphate; $P^1$-(6-eicosanyloxypurine riboside 5')-$P^4$-(uridine 5'-)tetraphosphate.

In addition, dinucleoside polyphosphates of general Formula III include dinucleoside triphosphates selected from the group consisting of: $P^1,P^3$-di(uridine 5'-)triphosphate; $P^1$-(cytosine 5')-$P^3$-(uridine 5'-)triphosphate; $P^1,P^3$-di(adenosine 5'-)triphosphate; $P^1$-(adenosine 5')-$P^3$-(uridine 5'-)triphosphate; $P^1$-(adenosine 5')-$P^3$-(cytosine 5'-)triphosphate; $P^{1,P3}$-di(ethenoadenosine)triphosphate; $P^1$-(uridine 5')-$P^3$-(thymidine 5'-)triphosphate; $P^1$-(adenosine 5')-$P^3$-(inosine 5'-)triphosphate; $P^1,P^3$-di(uridine 5'-)$P^2,P^3$-methylenetriphosphate; $P^1,P^3$-di(uridine 5'-$P^2,P^3$-difluoromethylenetriphosphate); $P^1,P^3$-di(uridine 5'-$P^2,P^3$-imidotriphosphate); $P^1,P^3$-di(4-thiouridine 5'-triphosphate); $P^1,P^3$-di(3,$N^4$-ethenocytidine 5'-)triphosphate; $P^1,P^3$-di(imidazo[1,2-c]pyrimidine-5(6H)-one-2-(3-nitro)-phenyl-6-β-D-ribofuranoside 5'-)triphosphate, $P^1$-(inosine 5'-)$P^3$-(uridine 5'-)triphosphate; $P^1$-(4-thiouridine 5'-)$P^3$-(uridine 5'-)triphosphate; $P^1$-(cytosine β-D-arabinofuranoside 5'-)$P^3$-(uridine 5')triphosphate; $P^1$-(uridine 5'-)$P^3$-(xanthosine 5'-)triphosphate; $P^1$-(2'-deoxyuridine 5'-)-$P^3$-(uridine 5'-)triphosphate; $P^1$-(3'-azido-3'-deoxythymidine 5'-)-$P^3$-(uridine 5'-)triphosphate; 2',3'-benzoyl-$P^1,P^3$-di(uridine 5'-)triphosphate; $P^1,P^3$-Di(2',3'-benzoyl uridine 5'-) triphosphate; $P^1$-(2'-deoxyguanosine 5'-)$P^3$-(uridine 5'-)triphosphate; $P^1$-(2'-deoxyadenosine 5'-)$P^3$-(uridine 5'-)triphosphate; $P^1$-(2'-deoxyinosine 5'-)$P^3$-(uridine 5'-)triphosphate; $P^1$-(2'-deoxycytidine 5'-)$P^3$-(uridine 5'-)triphosphate; $P^1$-(4-thiouridine 5'-)$P^3$-(uridine 5'-)triphosphate; $P^1$-(8-azaadenosine-5'-)$P^3$-(uridine 5'-)triphosphate; $P^1$-(6-mercaptopurine riboside 5'-)$P^3$-(uridine 5'-)triphosphate; $P^1$-(6-mercaptopurine riboside 5'-)$P^3$-(2'-deoxyuridine 5'-)triphosphate; $P^1$-(4-thiouridine 5'-)$P^3$-(arabinocytidine 5'-)triphosphate; $P^1$-(adenosine 5'-) $P^3$-(4-thiomethyluridine 5'-)triphosphate; $P^1$-(2'-deoxyadenosine 5'-)$P^3$-(6-thiohexylpurine riboside 5'-) tetraphosphate; and $P^1$-(6-eicosanyloxypurine riboside 5'-)$P^3$-(uridine 5'-) triphosphate.

Furthermore, dinucleoside polyphosphates of general Formula III include compounds selected from a group consisting of: $P^1$-(uridine 5'-)$P^2$-(4-thiouridine 5'-)diphosphate; $P^1,P^5$-di(uridine 5'-)pentaphosphate; and $P^1,P^6$-di(uridine 5'-)hexaphosphate.

A preferred nucleotide agonist is a hydrolysis-resistant agonist. One such class of hydrolysis-resistant agonists is a nucleotide with a modified phosphate backbone, e.g. an anologue which has a methylene, imido or other group that protects the phosphate bonds from being readily hydrolyzed. Dinucleotides are also resistant to hydrolysis due to a lack of a terminal phosphate group. Certain dinucleotides are especially resistant to hydrolysis. For example, $P^1$-(cytosine 5')-$P^4$-(uridine 5')tetraphosphate is more resistant in comparison with $P^1,P^4$-di(uridine 5'-)tetraphosphate. Furthermore, groups placed on the end of the phosphate chain imparts some stability against hydrolysis, e.g. simple alkyl phosphate esters (methyl, ethyl, benzyl, etc.) or a thio group (e.g. UTPgammaS). $UP_4U$ and $dCP_4U$ are preferred nucleotide receptor agonists.

Compounds encompassed by the preferred embodiment of the present invention can be prepared by condensation of a nucleoside mono-, di-, or triphosphate, activated with a condensing agent such as, but not limited to, carbonyldiimidazole or dicyclohexylcarbodiimide, with a second molecule of the same or a different mono-, di-, or triphosphate to form the desired dinucleotide polyphosphate. Another method of preparation is the sequential condensation of a nucleoside phosphate, activated as above, with a non-nucleoside mono-, di- or polyphosphate moiety, such as, but not limited to, a monophosphate or pyrophosphate anion to yield the desired dinucleotide polyphosphate, the non-isolated intermediate in such a case being a mononucleotide polyphosphate. Yet another preparative approach is the sequential condensation of a mono-, di- or polyphosphate moiety, activated as mentioned above, or in the form of an acid halide or other derivative reactive toward nucleophilic displacement, with a nucleoside phosphate or polyphosphate to yield the desired dinucleotide polyphosphate. The desired dinucleotide polyphosphate may be formed by modification of a pre-formed dinucleotide polyphosphate by substitution or derivatization of a moiety or moieties on the purine, pyrimidine or carbohydrate rings. Nucleoside phosphates used as starting materials may be commercially available, or may be made from the corresponding nucleosides by methods well known to those skilled in the art. Likewise, where nucleosides are not commercially available, they may be made by modification of other readily available nucleosides, or by synthesis from heterocyclic and carbohydrate precursors by methods well known to those skilled in the art.

Those having skill in the art will recognize that the starting materials may be varied and additional steps employed to produce compounds encompassed by this embodiment of the present invention, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The compounds of the present invention also encompass their non-toxic pharmaceutically acceptable salts, such as, but not limited to, alkali metal salts such as lithium, sodium or potassium; an alkaline earth metal salt such as magnesium or calcium; an ammonium or tetraalkyl ammonium salt, i.e., $NX_4^+$ (wherein X is $C_{1-4}$); or a mixed salts of the above. Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies, which may be employed to prepare non-toxic pharmaceutically acceptable salts and acylated prodrugs of the compounds (International Patent Nos. WO 96/40059, WO 96/02554A1, WO-A-9815563, and WO 98/55494; Theoclitou, et al., *J. Chem. Soc. Perkin Trans.* I, 2009-2019 (1996); Guranowski, et al., *Nucleosides and Nucleotides* 14, 731-734 (1995); Visscher, et al., *Nucleic Acids Research* 20, 5749-5752 (1992); Holler, et al., *Biochemistry* 22, 4924-4933 (1983); Orr, et al., *Biochem. Pharmacol.* 673-677 (1988); Plateau, et al., *Biochemistry* 24, 914-922 (1985); Hagmeier, et al., *J. Chromatography* 237, 174-177 (1982); Scheffzek, et al., *Biochemistry* 35, 9716-9727 (1996); Stridh, et al., *Antiviral Res.*, 97-105 (1981); Tarasova, et al., *Chem. Abs.* 110, 154770 (1988); Hata, et al., *Chem Lett.,* 987-990 (1976); Huhn, et al., 28, 1959-1970 (1993); Tumanov, et al., *Chem. Abs.* 109-6867d (1987); Pintor, et al., *Molecular Pharmacology* 51, 277-284 (1997); and U.S. Pat. Nos. 4,855,304; 5,635,160; 5,495,550; and 5,681,823).

The method of the present invention is useful to enhance the effects of pharmacotherapy and other methods currently used to treat and manage healing of allergy and inflammation. High doses may be required for some therapeutic agents to achieve levels to effectuate the target response, but may often be associated with greater frequency of dose-related adverse effects or increases the cost for the medication. Thus, combined use of the compounds of the present invention with agents commonly used to treat allergy and inflammation, such as antihistamines, decongestants, corticosteroids and sodium cromoglycate, permits relatively lower doses of such agents. Combined therapy results in a lower frequency of adverse side effects and lower cost associated with long-term administration of such therapeutic agents. Thus, in addition to enhancing safety, a combined therapeutic approach is also advantageous in increasing efficacy of treatment by enhancing the ability of a drug to reach its target site.

The pharmaceutical utility of compounds of this invention is indicated by the inositol phosphate assay for $P2Y_2$ and other P2Y receptor activity. This widely used assay, as described in Lazarowski, et al. (1995) (*Brit. J Pharm.* 116, 1619-27), relies on the measurement of inositol phosphate formation as a measurement of activity of compounds activating receptors linked via G-proteins to phospholipase C.

Therapeutic dosage levels at the site of action are of the order of from about $10^{-9}$ M to about $10^{-1}$ M, preferably in the range $10^{-6}$ to $10^{-1}$ M (U.S. Pat. Nos. 5,789,391; 5,900,407; 5,763,447; and PCT International Patent WO 00/30629). Calculations of the required dosage of administration to achieve therapeutic dose levels at the site of action can be determined by those skilled in the art, based on common knowledge of such parameters as volume of distribution at the site of action and expected bioavailability. For example, to achieve a therapeutic dosage level in the lung, the effective dose ranges between about 0.01 to about 1000 mg, preferably between about 0.1 to about 100 mg, and most preferably between about 0.5 to about 50 mg for single doses. For the ocular surface, a 50- to 1000-fold decrease in dosage is required to achieve commensurate therapeutic levels because the comparably smaller area of the ocular surface.

The amount of active ingredients that may be combined with the carrier materials to produce a single dosage form will vary depending upon the host treated and the particular mode of administration. It will be understood, however, that the specific dose level for any particular patient will depend upon a variety of factors, including the activity of the specific route of administration, and rate of excretion, drug combination and the severity of the particular disease undergoing therapy, and can be determined by those skilled in the art. Though the compounds of the present invention are primarily concerned with the treatment of human subjects, they may also be employed for the treatment of other mammalian subjects such as dogs and cats for veterinary purposes.

Administration of Compounds

Compound of Formula Ia, Ib, IIa, IIb, or III is formulated in a pharmaceutical formulation comprising the compound or pharmaceutically acceptable salts thereof, and optionally a pharmaceutically acceptable carrier. The pharmaceutical formulation is preferred to be a sterile formulation in some applications. The pharmaceutical formulation is administered to a subject by various routes of administration including topical, oral, parenteral, injection, intranasal, or intraocular routes to contact the site of inflammation and allergic reaction.

Topical administration includes the use of a solution, gel, suspension, cream, or ointment containing the active compound in a physiologically compatible vehicle. Gels or jellies may be produced using a suitable gelling agent including, but not limited to, gelatin, tragacanth, or a cellulose derivative and may include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Another method of topical administration is by delivery through the vagina. Pessaries are solid unit-dose forms suitably shaped for insertion into the vagina and may either be composed of a base that melts at body temperature or which dissolves when in contact with mucous secretions. Examples of suitable bases include, but are not limited to, theobroma oil, synthetic fat bases (e.g. Witepsol), polyethylene glycols (macrogols), and glycerol suppository basis. Vaginal tablets are composed of the active ingredient contained within a solid dosage form base which may include, but not be limited to, excipients such as lactose, microcrystalline cellulose, corn starch, magnesium stearate, silicon dioxide, and hydroxypropyl methylcellulose.

The compounds are administered systemically in a form selected from the group consisting of: an aerosol suspension of respirable particles; a liquid or liquid suspension for administration as nose drops or nasal spray; a nebulized liquid for administration to oral or nasopharyngeal airways; an oral form; an injectable form; a suppository form; and a transdermal patch or a transdermal pad; such that a therapeutically effective amount of said compound contacts the sites of allergic reactions and inflammation of said subject via systemic absorption and circulation One such means involve an aerosol mixture of respirable particles comprised of the active compounds, which the subject inhales. The therapeutic compound is absorbed into the bloodstream via the lungs in a pharmaceutically effective amount. The respirable particles may be liquid or solid, with a particle size sufficiently small to pass through the mouth and larynx upon inhalation; in general, particles ranging from about 1 to 10 microns, but more preferably 1-5 microns, in size are considered respirable.

Another means of delivering the therapeutic compound to sites of allergic reactions and inflammation involve administering a liquid/liquid suspension in the form of nasal drops of a liquid formulation, or a nasal spray of respirable particles which the subject inhales. Liquid pharmaceutical compositions of the active compound for producing a nasal spray or nasal drops are prepared by combining the active compounds with a suitable vehicle, such as sterile pyrogen free water or sterile saline by techniques known to those skilled in the art.

Other means of systemic administration of the active compound involve oral administration, in which pharmaceutical compositions containing compounds of Formulae Ia, Ib, IIa, IIb, and III are in the form of tablets, lozenges, aqueous or oily suspensions, dispersible powders or granules, emulsion, hard or soft capsules, syrups or elixirs or chewable gum. Compositions intended for oral use may be prepared according to any method known to the art; such compositions may contain one or more agents selected from the group consisting of sweetening agents, flavoring agents, coloring agents, and preserving agents in order to provide pharmaceutically elegant and palatable preparations. Tablets may be prepared to contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate, or sodium phosphate; granulating and disintegrating agents, for example, corn starch or alginic acid; binding agents, for example, starch, gelatin, or acacia; and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin, or olive oil.

The active compounds may also be delivered to sites of allergic reaction and inflammation of a subject through absorption by the skin using transdermal patches or pads. The active compounds are absorbed into the bloodstream through the skin. Plasma concentration of the active compounds can be controlled by using patches containing different concentrations of active compounds.

Additional means of systemic administration of the active compound to sites of allergic reaction and inflammation of the subject involve a suppository form of the active compound, such that a therapeutically effective amount of the compound reaches sites of allergic reaction and inflammation via systemic absorption and circulation.

Another means of administering the active compound would involve direct intra-operative instillation of a gel, cream, or liquid suspension form of a therapeutically effective amount of the active compounds.

The invention is illustrated further by the following examples of treatment which are not to be construed as limiting the scope of the specific procedures describing them.

EXAMPLES

Example 1

Effects of $UP_4U$ on Ocular Type-1 Hypersensitivity in Albino Rats (Topical 48/80 Model)

The rat model of ocular immediate (Type-1) hypersensitivity using topical compound 48/80 was used for testing anti-inflammatory drugs (Feinberg and Stokes, *Int. Arch. Allergy Appl. Immunol.* 82(3-4): 537-8. (1987)). The effects of levocabastine, ketotifen, and olopatadine, which are three approved drugs for the use of ocular surface inflammation, particularly allergic conjunctivitis, were assessed.

$UP_4U$ was investigated for its effects on mitigating the clinical signs of compound 48/80 on ocular surface type-1 hypersensitivity. Ten albino rats per group were administered compound or vehicle four times daily for 3 days and twice on the fourth day (the last administration 2 h before challenge with 48/80). Comparison was made between the test substances, the test substances vehicle, the reference substance (0.05% levocabastine eye drops—Lévophta®; 0.025% ketotifen eyedrops—Zaditor®; and 0.1% olopatadine eyedrops—Patanol™), and negative control animals (untreated and unchallenged).

Eye drops were instilled into the right conjunctival sac of each animal with test substances. The formulated compounds or vehicle were administered to the most superior available part of the eyeball, after raising the eyelid, via 10 μL administration with a micropipette. The formulated compounds or vehicle were allowed to gradually run from the top to the bottom of the ocular surface. Efficacy was evaluated by measuring edema: clinical scores and extravasation of Evans blue dye (blood-eyelids and blood-eyeballs permeability indexes). The model has been previously validated (Khosravi, et al., *Inflamm. Res.* 44(1): 47-54 (1995)).

Figure 1:
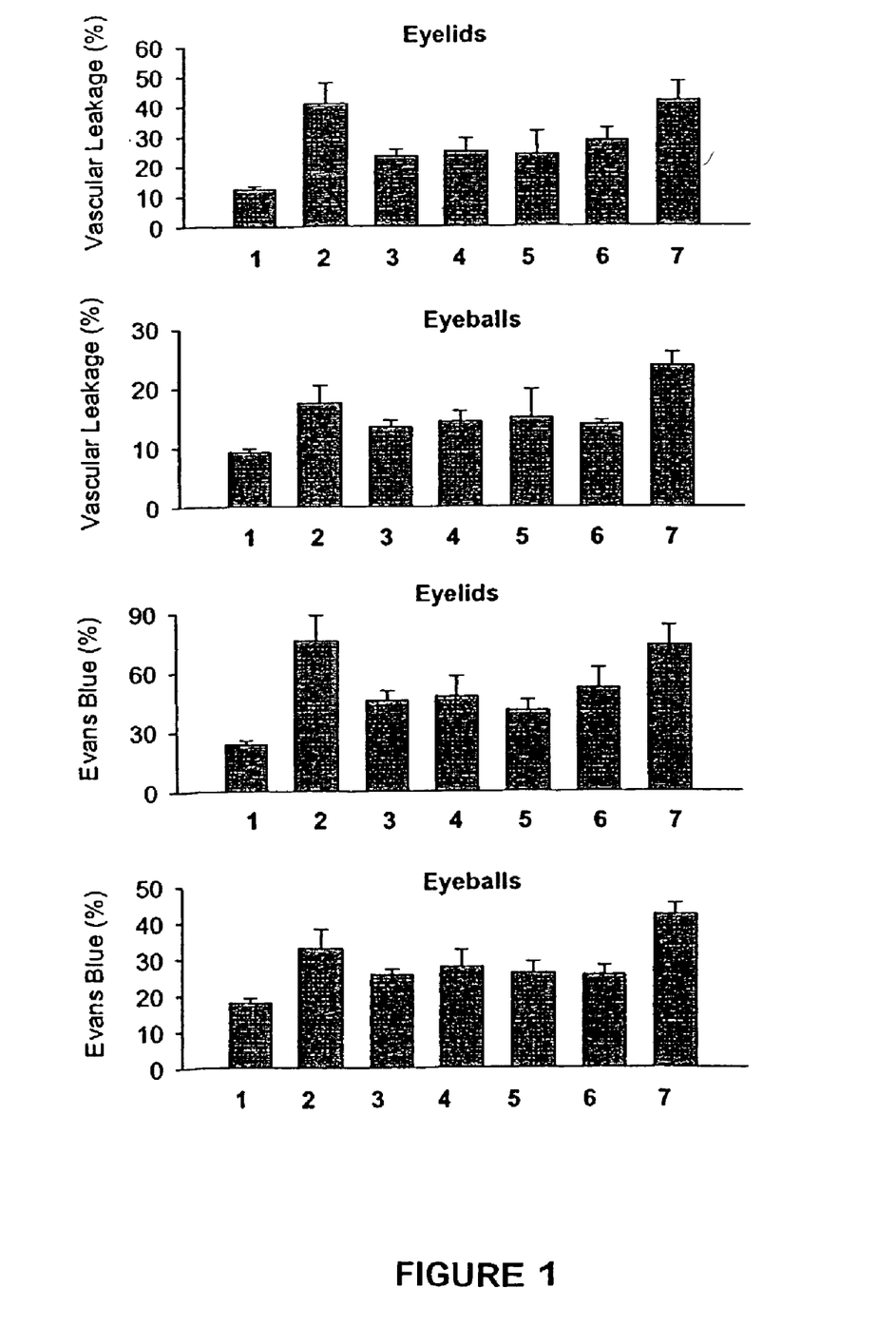
FIG. 1 shows the effects of (1) untreated, (2) 48/80 alone, (3) 0.05% levocabastine, (4) 0.025% ketotifen, (5) 0.1% olopatadine, (6) 2% $UP_4U$ and (7) vehilceon vascular leakage and Evans Blue extravasation on eyelids and eyeballs in rats treated with on the ocular surface.

FIG. 1 shows that $UP_4U$ reduced vascular leakage and Evans blue extravasation on eyelids and eyeballs in rats treated with 48/80 on the ocular surface. The magnitude of $UP_4U$-induced reduction in these parameters were comparable with the three reference controls, levocabastine, ketotifen, and olopatadine.

Example 2

Effects of $UP_4U$ on Active Anaphylaxis After Multiple Administrations Using the Guinea Pig Egg Albumin Model The guinea pig model of ocular active anaphylaxis with egg albumin as an antigen, serves as a testing system for anti-inflammatory and anti-allergic drugs (Yamaji, et al., *Methods Find. Exp. Clin. Pharmacol.* 19(9): 637-43 (1997)). The ocular effects of compounds and vehicle control were investigated using an experimentally-induced ocular active anaphylaxis in the guinea pig.

Ten albino guinea pigs per group were sensitized with an intraperitoneal injection of egg albumin, followed 14 days later with a challenge by a single ocular instillation of egg albumin. Four times daily for 3 days and twice on the fourth day (the last one 2 h before challenge), test substances were instilled into the right conjunctival sac of the animals. The immune response was induced by immunization with egg albumin, and the ocular reaction was induced by ocular instillation of egg albumin, thereby causing the release of allergy mediators and ocular edema.

Efficacy was evaluated by measuring edema: clinical scores and extravasation of Evans blue dye (blood-eyelids and blood-eyeballs permeability indexes). Comparison was made between the test substances, the test substances vehicle, the reference substance (0.05% levocabastine eye drops—Lévophta®; 0.025% ketotifen eyedrops—Zaditor®; and 0.1% olopatadine eyedrops—Patanol™), and negative control animals (untreated and unchallenged). The model was previously validated (Khosravi, et al., *Inflamm. Res.* 44(1): 47-54 (1995)).

Figure 2:
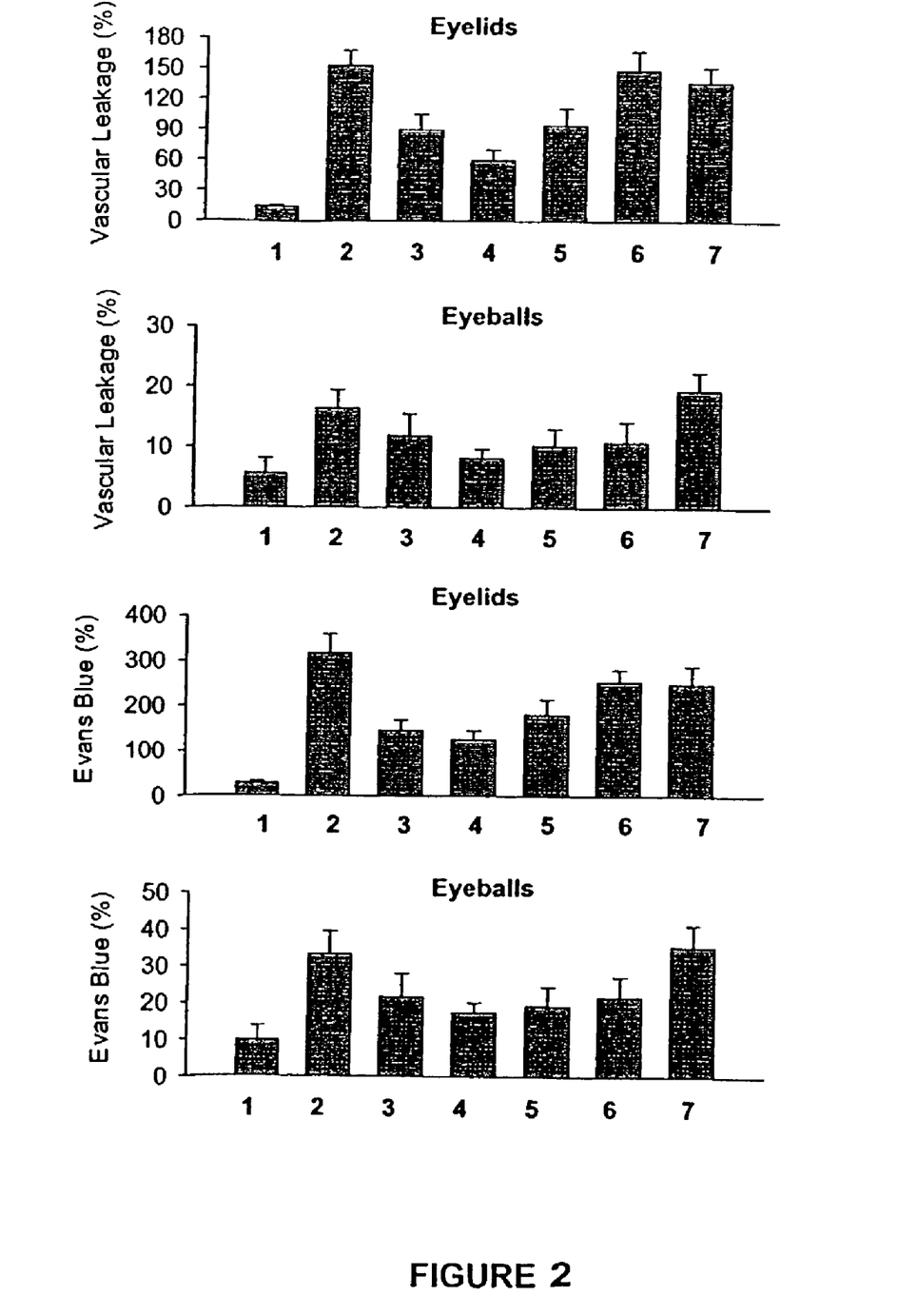
FIG. 2 shows the effects of (1) untreated, (2) 48/80 alone, (3) 0.05% levocabastine, (4) 0.025% ketotifen, (5) 0.1% olopatadine, (6) 2% $UP_4U$ and (7) vehicle on vascular leakage and Evans Blue extravasation on eyelids and eyeballs in guinea pigs challenged with egg albumin.

FIG. 2 shows that $UP_4U$ reduced vascular leakage and Evans blue extravasation on eyeballs, but not eyelids, in guinea pigs challenged with egg albumin. The magnitude of $UP_4U$-induced reduction in these parameters on eyeballs was comparable with the three reference controls, levocabastine, ketotifen, and olopatadine.

Thus, in two in vivo models of allergic conjunctivitis, the P2Y agonist $UP_4U$ was shown to counteract proinflammatory markers. These novel findings are inconsistent with prior art observations which teach pro-inflammatory effects of nucleotide receptor agonists.

Example 3

Effects of UP$_4$dC on Nasal Tissue in Humans
(Nasal Spray STT Test)

This example illustrates nasal spray results in humans using the saccharin transport time (STT) test. The STT involved placing a small particle of saccharin on the inferior turbinate in the nose and then evaluating the elapsed time from placement in the nose until the taste is detected on the tongue in the posterior pharynx. The speed with which the saccharin was transported this distance is a measure of mucociliary clearance.

Sixty subjects, 30 healthy non-rhinitic (NR) volunteers and 30 subjects with perennial allergic rhinitis (PAR), participated in a randomized, double-blind, single-center, 2-period crossover study evaluating escalating, single doses of a UP$_4$dC nasal spray delivered as a non-preserved aqueous nasal spray. Each subject received a single dose (2 sprays in each nostril, 140 µL/spray) of UP$_4$dC and placebo (0.9% w/v saline spray) on two treatment days in random order (crossover design). Five cohorts of 12 subjects received five concentration levels of UP$_4$dC (5, 10, 20, 40, and 80 mg/mL) in ascending order. The STT was performed 5-minutes and 300-minutes post-dose on each treatment day on each subject (a saccharin particle was placed in the nose at 5 and 300 minutes post-dose and then time to taste was recorded).

The UP$_4$dC treatment was observed to shorten the time elapsed before the saccharin was tasted compared to placebo, illustrating that UP$_4$dC enhanced mucociliary clearance. When pooled across strata (PAR and NR combined) and across doses of UP$_4$dC, the mean STT for the UP$_4$dC treated subjects was 7.04 (±6.06) and 9.58 (±10.30) minutes at the 5-minute and 5-hour (300-minute) assessment, respectively, compared to 8.60 (±7.37) and 12.92 (±13.29) minutes for the placebo-treated subjects at the same time points. Analyses were carried out excluding those STT values that were either too fast (<1 minute) or too slow (>30 minutes). Both of these scenarios are deemed as errors and are a likely result of the saccharin particle being inappropriately administered. Displayed in Table 1 are the results of this analysis in which the outlier values have been removed.

TABLE 1

STT Across all Cohorts-NR and PAR groups pooled (without outliers)

| STT | UP$_4$dC | Placebo | P value UP$_4$dC vs. placebo |
|---|---|---|---|
| 5 minute | | | |
| number of subjects | 57 | 58 | |
| mean (± SD) | 6.89 (5.36) | 8.58 (7.88) | 0.197 |
| 300 minute | | | |
| number of subjects | 55 | 56 | |
| mean (± SD) | 8.41 (5.79) | 10.88 (9.26) | 0.074 |

The results above clearly illustrate a pharmacological effect of a UP4dC nasal spray in enhancing mucociliary clearance in the nose. This is illustrated in the results, both with and without outliers.

Example 4

Effects of UP$_4$dC on Perennial Allergic Rhinitis
Symptoms in Humans

This example illustrates the efficacy of a UP$_4$dC nasal spray in reducing the symptoms of perennial allergic rhinitis (PAR) in humans. Patients with PAR suffer year-round from symptoms of allergic rhinitis because they are sensitized to allergens that are present in homes and the environment throughout the year, including dust mites, molds, and animal danders (dogs, cats, cockroaches, etc). Patients with PAR experience a constellation of nasal symptoms including nasal stuffiness/congestion, runny nose, post-nasal drip, sneezing and nasal itching. These symptoms were evaluated in pivotal efficacy trials as the total nasal symptom score (TNSS) as well as by evaluating each individual symptom, including the non-nasal symptoms of facial pain/pressure and cough. Patients rated each individual symptom on a scale from 0 (none) to 3 (severe) twice daily, reflecting their symptoms upon awakening (AM) and throughout the day (PM).

Fifty-nine subjects with a documented history of PAR participated in a randomized, double-blind, 3-center, parallel-group study. After demonstrating moderate to severe symptom severity during a single-blind placebo run-in period, subjects were randomly assigned to one of three concentrations of the UP$_4$dC nasal spray (5 mg/mL, 10 mg/mL, and 40 mg/mL) or placebo (0.9% w/v saline spray) for 6 days. Study medication was delivered twice daily as a non-preserved aqueous nasal spray as 2 sprays (100 µL in each spray) in each nostril.

The change from the placebo run-in period with respect to the TNSS averaged over the entire 6-day treatment period is displayed in Table 2. While none of three groups receiving the active compound UP$_4$dC achieved a statistically significant separation from placebo, the active treatment groups experienced consistently greater reductions in TNSS compared with placebo for AM, PM, and AM+PM analyses. This was most notable for the 10 mg/ml UP$_4$dC group. Comparisons of pooled active versus placebo TNSS scores approached statistical significance for AM scores (p=0.139).

TABLE 2

| Assessment | Placebo | 5 mg/mL UP$_4$dC | 10 mg/mL UP$_4$dC | 40 mg/mL UP$_4$dC |
|---|---|---|---|---|
| AM (0–15 scale) | 0.02 (1.88) | −0.96 (2.08) | −1.20 (2.00) | −1.14 (2.02) |
| PM (0–15 scale) | −0.44 (1.79) | −0.94 (2.07) | −1.26 (2.46) | −1.01 (2.55) |
| AM + PM (0–30 scale) | −0.61 (3.82) | −2.02 (4.31) | −2.59 (4.50) | −2.09 (3.99) |

Statistically significant reductions in TNSS, total symptom scores (all symptoms—nasal plus non-nasal), and individual symptoms were noted on individual days and with individual doses. These results are still surprising for such a small sample group.

Table 3 indicates the symptom and dose combinations that provided statistically significant reductions (p≦0.05) compared with placebo on any day during the 6-day treatment period. Conversely, significant symptom reductions in favor of placebo were observed on one day (PM sneezing, Day 2).

TABLE 3

| Symptom | 5 mg/mL UP₄dC | 10 mg/mL UP₄dC | 40 mg/mL UP₄dC |
|---|---|---|---|
| TNSS |  | AM-Day 6 PM-Day 5 | AM-Day 3 |
| Total Symptom Score |  | AM-Days 5 and 6 | PM-Day 5 |
| Nasal blockage/stuffiness | AM-Day 4 | AM-Day 5 |  |
| Post-nasal drip | AM-Days 4 and 6 | AM-Days 5 and 6 | AM-Day 5 PM-Day 5 |
| Rhinorrhea |  | PM-Day 5 |  |
| Itching |  | AM-Day 6 PM-Day 6 | AM-Day 3 |
| Facial pain/pressure | AM-Days 1–3, 5 PM-Days 1 and 2 | AM-Days 2, 5–6 PM-Day 1 |  |
| Sneezing |  |  |  |
| Cough |  |  |  |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of treating an inflammatory disease, said method comprising:
    administering to a subject suffering from an inflammatory disease a pharmaceutical formulation comprising a P2Y receptor agonist in an amount effective to treat the inflammatory disease, wherein said inflammatory disease is selected from the group consisting of rhinitis, conjunctivitis, asthma, dermatitis, inflammatory bowel disease, inflammatory collagen vascular diseases, glomerulonephritis, inflammatory skin diseases, sarcoidosis, and an inflammatory disease caused by infection or allergy, wherein said P2Y receptor agonist is a dinucleoside polyphosphate where the polyphosphate is in between the two nucleosides.

2. The method according to claim 1, wherein said treating is alleviating symptoms and manifestations of said inflammatory disease.

3. The method according to claim 1, wherein said inflammatory disease caused by allergy is allergic rhinitis, allergic dermatitis, or allergic conjunctivitis.

4. The method according to claim 3, wherein said allergic rhinitis is perennial allergic rhinitis, seasonal allergic rhinitis, or infectious allergic rhinitis.

5. The method according to claim 3, wherein said inflammatory disease is allergic conjunctivitis.

6. The method according to claim 1, wherein said P2Y receptor agonist is a dinucleoside polyphosphate of Formula III, or a pharmaceutically acceptable salt thereof:

Formula III wherein:
X is oxygen, methylene, dihalomethylene, or imido;
n=0, 1 or 2;
m=0, 1 or 2;
n=m=1, 2,3 or 4;
Z=H or OH;
Z'=H or OH;
Y=H or OH;
Y'=H or OH;
wherein at least one of Z, Z', Y, or Y' is OH; and
B and B' are each independently a purine residue or a pyrimidine residue, as defined in Formula IIIa and IIIb, respectively, linked through the 9- or 1-position, respectively:

Formula IIIa wherein:
  $R_{11}$ is hydrogen, chlorine, amino, monosubstituted amino, disubstituted amino, alkylthio, arylthio, or aralkylthio, where the substituent on sulfur contains up to a maximum of 10 carbon atoms, with or without unsaturation;
  $R_{12}$ is hydroxy, alkenyl, oxo, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, or diacylamino;
  $R_x$ is O, H or absent;
  $R_{12}$ and $R_x$ are optionally taken together form a 5-membered fused imidazole ring of 1, $N^6$-ethenoadenine derivatives, optionally substituted on the 4- or 5- positions of the etheno moiety with alkyl, aryl, nitroaryl, haloaryl, aralkyl or alkoxy moieties;
  $R_{13}$ is hydrogen, azido, alkoxy, aryloxy, aralkyloxy, alkylthio, arylthio, or aralkylthio, or T(C1.6 alkyl)OCONH ($C_{1-6}$ alkyl)W—wherein T and W are independently amino, mercapto, hydroxy or carboxyl; or pharmaceutically acceptable esters, amides or salts thereof; or absent; and
  J is carbon or nitrogen, with the provision that when J is nitrogen, $R_{13}$ is not present;

Formula IIIb wherein:
  $R_{14}$ is oxo, hydroxy, mercapto, thione, amino, cyano, $C_{7-12}$ arylalkoxy, $C_{1-6}$ alkylthio, $C_{1-6}$ alkoxy, $C_{1-6}$ alkylamino or $diC_{1-4}$ alkylamino, wherein the alkyl groups are optionally linked to form a heterocycle;

$R_{15}$ is hydrogen, acetyl, benzoyl, alkyl, acyl, arylacyl, arylalkyl, $_{1-5}$ alkanoyl, aroyl, or is absent when there is a double bond between N-3 and C-4;

$R_{16}$ is hydroxy, oxo, mercapto, thione, $C_{1-4}$ alkoxy, $C_{7-12}$ arylalkoxy, $C_{1-6}$ alkylthio, S-phenyl, arylthio, aralkylthio, arylalkylthio, triazolyl, amino, $C_{1-5}$ disubstituted amino, $C_{1-6}$ alkylamino, or di-$C_{1-4}$ alkylamino wherein said dialkyl groups are optionally linked to form a heterocycle or linked to form a substituted ring; or $R_{15}$ and $R_{16}$ taken together form a 5-membered fused imidazole ring of 3, $N^4$-ethenocytosine derivatives between positions 3 and 4 of the pyrimidine ring, wherein said etheno moiety is optionally substituted on the 4- or 5-positions with $C_{1-4}$ alkyl, phenyl, arylalkyl, or nitrophenyl;

$R_{17}$ is hydrogen, hydroxy, cyano, nitro, $C_{1-6}$ alkyl, $C_{2-8}$ alkenyl, $C_{2-8}$ alkynyl, phenyl, halogen, $CF_3$, allylamino, bromovinyl, ethyl propenoate, propenoic acid; or $R_{16}$ and $R_{17}$ together form a 5 or 6-membered saturated or unsaturated ring bonded through N or O or S at $R_{16}$, said ring optionally contains functional substituents; and $R_{18}$ is hydrogen, amino, alkylamino, acylamino, di-$C_{1-4}$ alkylamino, $C_{1-4}$ alkoxy, $C-_{7-12}$ arylalkoxy, $C_{1-4}$ alkylthio, $C_{7-12}$ arylalkylthio, carboxamidomethyl, carboxymethyl, methoxy, methylthio, phenoxy, or phenylthio; provided that when $R_{18}$ is amino or substituted amino, $R_{17}$ is hydrogen;

wherein the alkyl, alkenyl, alkynyl, and aryl groups are optionally substituted with lower alkyl, aryl, amino, mono- or dialkylamino, $NO_2$, $N_3$, cyano, hydroxy, carboxylic, amido, sulfonamido, sulphonic acid, phosphate, or halo groups.

7. The method according to claim 6, wherein the sugar moiety of Formula III is a furanosyl or deoxyfuranosyl moiety.

8. The method according to claim 7, wherein the sugar moiety is selected from the group consisting of: ribofuranosyl, 2'-deoxyribofuranosyl, 3'-deoxyfuranosyl, 2',3'-dideoxyribofuranosyl, arabinofuranosyl, 3'-deoxyarabinofuranosyl, xylofuranosyl, 2'-deoxyxylofuranosyl and lyxofuranosyl.

9. The method according to claim 6, wherein said dinucleoside polyphosphate of general Formula III is a dinucleoside tetraphosphate selected from the group consisting of $P^1,P^4$-di(uridine 5'-)tetraphosphate; $P^1$-(cytidine 5')-$P^4$-(undine 5'-)tetraphosphate; $P^1,P^4$-di(adenosine 5'-)tetraphosphate; $P^1$-(adenosine 5')-$P^4$-(uridine 5'-)tetraphosphate; $P^1$-(adenosine 5')-$P^4$-(cytidine 5'-)tetraphosphate; $P^1,P^4$-di(ethenoadenosine)tetraphosphate; $P^1$-(uridine 5')-$P^4$-(thymidine 5'-)tetraphosphate; $P^1$-(adenosine 5')-$P^4$-(inosine 5'-)tetraphosphate; $P^1,P^4$-di(uridine 5')-$P^2,P^3$-methylenetetraphosphate; $P^1,P^4$-di(uridine 5')-$P^2,P^3$-difluoromethylenetetraphosphate; $P^1,P^4$-di(uridine 5')-$P^2,P^3$-imidotetraphosphate; $P^1,P^4$-di(4-thiouridine 5'-)tetraphosphate; $P^1,P^5$-di(uridine 5'-)pentaphosphate; $P^1,P^4$-di(3, $N^4$-ethenocytidine 5'-)tetraphosphate; $P^1,P^4$-di(imidazo[1,2-c]pyrimidine-5(6H)-one-2-(3-nitro)-phenyl-6-β-D-ribofuranoside 5'-)tetraphosphate; $P^1$-(inosine 5')-$P^4$-(uridine 5'-)tetraphosphate; $P^1$-(cytosine β-D-arabinofuranoside 5')-$P^4$-(uridine 5'-)tetraphosphate; $P^1$-(uridine 5')-$P^4$-(xanthosine 5'-)tetraphosphate; $P^1$-(2'-deoxyuridine 5')-P4-(uridine 5'-)tetraphosphate; $P^1$-(3'-azido-3'-deoxythymidine 5')-$P^4$-(uridine 5'-)tetraphosphate; $P^1,P^4$-di(3'-azido-3'-deoxythymidine 5'-)tetraphosphate; 2'(3')-benzoyl-$P^1,P^4$-di(uridine 5'-)tetraphosphate; $P^1,P^4$-di[2',(3')-benzoyl uridine 5'-]tetraphosphate; $P^1$-(2'-deoxyguanosine 5')-$P^4$-(uridine 5'-)tetraphosphate; $P^1$-(2'-deoxyadenosine 5')-$P^4$-(uridine 5'-)tetraphosphate; $P^1$-(2'-deoxyinosine 5')-$P^4$-(uridine 5'-) tetraphosphate; $P^1$-(2'-deoxycytidine 5')-$P^4$-(uridine 5'-)tetraphosphate; P'-(4-thiouridine 5')-$P^4$-(uridine 5'-)tetra-phosphate; $P^1$-(8-azaadenosine 5')-$P^4$-(uridine 5'-)tetraphosphate; $P^1$-(6-mercaptopurine riboside 5')-$P^4$-(uridine 5'-)tetraphosphate; $P^1$-(6-mercaptopurine riboside 5')-$P^4$-(2'-deoxyuridine 5'-) tetraphosphate; $P^1$-(4-thiouridine 5')-$P^4$-(cytosine-β-D-arabinofuranoside 5'-)tetraphosphate; $P^1$-(adenosine 5')-$P^4$-(4-thiomethyluridine 5'-)tetraphosphate; $P^1$-(2'-deoxyadenosine 5')-$P^4$-(6-thiohexylpurine riboside 5'-) tetraphosphate; and $P_1$-(6-eicosanyloxypurine riboside 5')-$P^4$-(uridine 5'-)tetraphosphate.

10. The method according to claim 9, wherein said P2Y receptor agonist is selected from the group consisting of: $P^1$-(2'-deoxycytidine 5')-$P^4$-(uridine 5'-)tetraphosphate; $P^1,P^4$-di(uridine 5'-)tetraphosphate; P'-(adenosine 5')- $P^4$-(uridine 5'-)tetraphosphate; $P^1$-(adenosine 5')-P4-(inosine 5'-)tetraphosphate; $P^1,P^4$-di(uridine 5')-$P^2,P^3$-difluoromethylenetetraphosphate; $P^1,P^4$-di(4-thiouridine 5'-)tetraphosphate; $P^1$-(inosine 5')-$P^4$-(uridine 5'-)tetraphosphate; $P^1$-(2'-deoxyuridine 5')-$P^4$-(uridine 5'-)tetraphosphate; $P^1$-(2'-deoxyguanosine 5')-$P^4$-(uridine 5'-)tetraphosphate; $P^1$-(2'-deoxyinosine 5')-$P^4$-(uridine 5'-)tetraphosphate; $P^1$-(4-thiouridine 5')-$P^4$-(uridine 5'-)tetraphosphate; and $P^1$-(adenosine 5')-P4-(4-thiomethyluridine 5'-)tetraphosphate.

11. The method according to claim 10, wherein said P2Y receptor agonist is selected from the group consisting of: $P^1$-(2'-deoxycytidine 5+)-$P^4$-(uridine 5'-)tetraphosphate; $P^1,P^4$-di(uridine 5'-)tetraphosphate; $P^1$-(adenosine 5')-P4-(uridine 5'-)tetraphosphate; $P^1$-(inosine 5')-$P^4$-(uridine 5'-) tetraphosphate; $P^1$-(2'-deoxyguanosine 5')-$P^4$-(uridine 5'-) tetraphosphate; and $P^1$-(2'-deoxyinosine 5')-$P^4$-(uridine 5'-) tetraphosphate.

12. A method of treating an inflammatory disease, said method comprising: administering to a subject a pharmaceutical formulation comprising a P2Y receptor agonist in an amount effective to treat the inflammatory disease, whereis said P2Y receptor agonist is a dinucleoside triphosphate selected from the group consisting of:

$P^1P^3$-di(uridine 5'-)triphosphate; $P^1$-(cytosine 5')-$P^3$-(uridine 5'-)triphosphate; $P^1,P^3$-di(adenosine 5'-)triphosphate; $P^1$-(adenosine 5')-$P^3$-(uridine 5'-)triphosphate; $P^1$-(adenosine 5')-$P^3$-(cytosine 5'-)triphosphate; $P^1,P^3$-di(ethenoadenosine)triphosphate; $P^1$-(uridine 5')-$P^3$-(thymidine 5'-)triphosphate; $P^1$-(adenosine 5')-$P^3$-(inosine 5 '-)triphosphate; $P^1,P^3$-di(uridine 5'-)$P^2,P^3$-methylenetriphosphate; $P^1,P^3$-di(uridine 5'-$P^2,P^3$-difluoromethylenetriphosphate); $P^1,P^3$-di(uridine 5'-$P^2$, $P^3$-imidotriphosphate); $P^1,P^3$-di(4-thiouridine 5'-triphosphate); $P^1,P^3$-di(3,$N^4$-ethenocytidine 5'-) triphosphate; $P^1,P^3$-di(imidazo[1,2-c]pyrimidine-5 (6H)-one-2-(3-nitro)-phenyl-6-β-D-ribofuranoside 5'-) triphosphate; $P^1$-(inosine 5'-)$P^3$-(uridine 5'-) triphosphate; $P^1$-(4-thiouridine 5'-)$P^3$-(uridine 5'-) triphosphate; $P^1$-(cytosine β-D-arabinofuranoside 5'-) $P^3$-(uridine 5')triphosphate; $P^1$-(uridine 5'-)$P^3$-(xanthosine 5'-)triphosphate; $P^1$-(2'-deoxyuridine 5'-)-$P^3$-(uridine 5'-)triphosphate; $P^1$-(3'-azido-3'-deoxythymidine 5'-)-$P^3$-(uridine 5'-)triphosphate; $P^1,P^3$-di(3'-azido-3'-deoxythymidine 5'-)triphosphate; 2'(3')-benzoyl-$P^1,P^3$-di(uridine 5'-)triphosphate; $P^1,P^3$-di(2',3'-benzoyl uridine 5'-)triphosphate; P'-(2'-deoxyguanosine 5'-)$P^3$-(uridine 5'-)triphosphate; $P^1$-(2'-deoxyadenosine 5'-)$P^3$-(uridine 5'-)triphosphate; $P^1$-(2'-deoxyinosine 5'-)$P^3$-(uridine 5'-)triphosphate; $P^1$-

(2'-deoxycytidine 5'-)$P^3$-(uridine 5'-)triphosphate; $P^1$-(4-thiouridine 5'-) $P^3$-(uridine 5'-) triphosphate; $P^1$-(8-azaadenosine-5'-)$P^3$-(uridine 5'-)triphosphate; $P^1$-(6-mercaptopurine riboside 5'-)$P^3$-(uridine 5'-) triphosphate; $P^1$-(6-mercaptopurine riboside 5'-) $P^3$-(2'-deoxyuridine 5'-)triphosphate; $P^1$-(4-thiouridine 5'-)$P^3$-(arabinocytidine 5'-)triphosphate; $P^1$-(adenosine 5'-)$P^3$-(4-thiomethyluridine 5'-)triphosphate; $P^1$-(2'-deoxyadenosine 5'-)$P^3$-(6-thiohexylpurine riboside 5'-)tetraphosphate; and $P^1$-(6-eicosanyloxypurine riboside 5'-)$P^3$-(uridine 5'-)triphosphate.

13. A method of treating an inflammatory disease, said method comprising: administering to a subject a pharmaceutical formulation comprising a P2Y receptor agonist in an amount effective to treat the inflammatory disease, wherein said P2Y receptor agonist is selected from the group consisting of: $P^1$-(uridine 5'-)$P^2$-(4-thiouridine 5'-)diphosphate; $P^1,P^5$-di(uridine 5'-)pentaphosphate; and $P^1,P^6$-di(uridine 5'-)hexaphosphate.

14. The method according to claim 1, wherein said administering is topical administering a form selected from the group consisting of a solution, a gel, a suspension, a cream, and an ointment containing the active compound in a physiologically compatible vehicle.

15. The method according to claim 1, wherein said administering is systemically administering a form selected from the group consisting of an aerosol suspension of respirable particles, a liquid or liquid suspension for administration as nose drops or nasal spray, a nebulized liquid for administration to oral or nasopharyngeal airways, an oral form, an injectable form, a suppository form, and a transdermal patch or a transdermal pad.

16. The method according to claim 1, wherein said administering is direct intra-operative instilling a form selected from the group consisting of a gel, a cream, and a liquid suspension form.

17. The method according to claim 6, wherein said inflammatory disease is allergic rhinitis, allergic dermatitis, or allergic conjunctivitis.

18. The method according to claim 1, wherein said inflammatory disease is caused by upper respiratory infection.

* * * * *